United States Patent [19]

Berry, Jr.

[11] Patent Number: 4,825,259
[45] Date of Patent: Apr. 25, 1989

[54] ADAPTER TIP FOR REMOTE MEASURING DEVICE

[76] Inventor: Robert F. Berry, Jr., Rte. 3, Box 259, Hayes, Va. 23072

[21] Appl. No.: 151,863

[22] Filed: Feb. 3, 1988

[51] Int. Cl.$^4$ .................. G02B 23/26; G01B 11/02
[52] U.S. Cl. ............................. 356/241; 128/6; 356/383; 356/397
[58] Field of Search ............... 356/241, 383, 384, 397; 128/4, 6

[56] References Cited

U.S. PATENT DOCUMENTS

| | | | |
|---|---|---|---|
| 3,595,220 | 8/1968 | Kawahara | 128/6 |
| 3,730,632 | 5/1973 | Chikama | 128/6 X |
| 3,817,635 | 6/1974 | Kawahara | 128/6 X |
| 3,819,267 | 6/1974 | Kawahara | 128/6 X |
| 4,078,864 | 3/1978 | Howell | 356/241 |
| 4,558,691 | 12/1985 | Okada | 128/6 |
| 4,588,294 | 5/1986 | Siegmund | 356/241 |
| 4,660,982 | 4/1987 | Okada | 356/383 |
| 4,727,859 | 3/1988 | Lia | 728/6 |

Primary Examiner—Vincent P. McGraw
Attorney, Agent, or Firm—Harold W. Adams; John R. Manning; Charles E. B. Glenn

[57] ABSTRACT

The invention is an adapter tip 11 for supporting measuring indicia 22 on the forward end 12 of a conventional optical borescope 14 including focus adjustment means thereby permitting the substantially direct, physical measurement of internal surfaces and defects inside an object such as a pressure vehicle having an external opening therein when said measuring indicia 22 are positioned to coincide with a surface orb defect to be measured and simultaneously brought into focus with said surface or defect with said focus adjustment means.

10 Claims, 2 Drawing Sheets

ADAPTER TIP FOR REMOTE MEASURING DEVICE

ORIGIN OF THE INVENTION

The invention described herein was made by an employee of the United States Government and may be manufactured and used by or for the Government for governmental purposes without the payment of any royalties thereon or therefor.

BACKGROUND OF THE INVENTION

1. Field of the Invention

The invention relates to an adapter tip for supporting a suitable scale and which fits on the forward end of a conventional borescope or similar remote measuring device permitting substantially direct and external physical measurement of internal surfaces and defects inside an object such as a pressure vehicle or the like.

2. Description of the Prior Art

Optical measuring devices such as the Olympus Fiberscope manufactured by the Industrial Fiber Optics Division, Olympus Corporation, 4 Nevada Dr., Lake Success, N.Y. 11042, are commercially available. Typically as with this and other similar optical devices, measurement accuracy is dependent upon the distance between the object and the sensor used. A number of U.S. patents have issued generally disclosing optical endoscopes for measuring internal dimensions through an opening in a chamber, organ or the like from the forward end of the device. For instance, see U.S. Pat. Nos. 4,558,691, 3,817,635, 3,819,267, 3,595,220, 3,730,632 and 4,588,294.

None of these prior art devices provide an adapter tip for a borescope or similar device that permits a remote or external substantially direct measurement of internal dimensions and defects in an object through an opening in the object.

OBJECTS AND SUMMARY OF THE INVENTION

An object of the invention is to provide an adapter tip for the forward end of a remote measuring device such as a borescope that provides a suitable scale permitting substantially the direct and external physical measurement of an internal surface or defect when the adapter scale is positioned within the field of view of the borescope and both the scale and surface or defect to be measured are simultaneously brought into focus.

A further object is to provide such an adapter tip that may be readily attached and removed.

Still another object is to provide such an adapter tip that may be formed of rigid or bendable materials and provide a plurality of different scales and measuring indicia.

The above and numerous other objects and advantages are obtained by the invention which provides an adapter tip that may be detachably secured to the forward end or an extension of a borescope or similar device for internally examining the interior of an object and which provides a suitable scale thereon permitting substantially a direct visual measurement of a surface or defect within the object.

BRIEF DESCRIPTION OF THE DRAWINGS

The above and numerous other objects and advantages will become apparent from the following Detailed Description of a Preferred Embodiment of the Invention when read in light of the accompanying drawings wherein.

BRIEF DESCRIPTION OF A PREFERRED EMBODIMENT OF THE INVENTION

Figure 1:
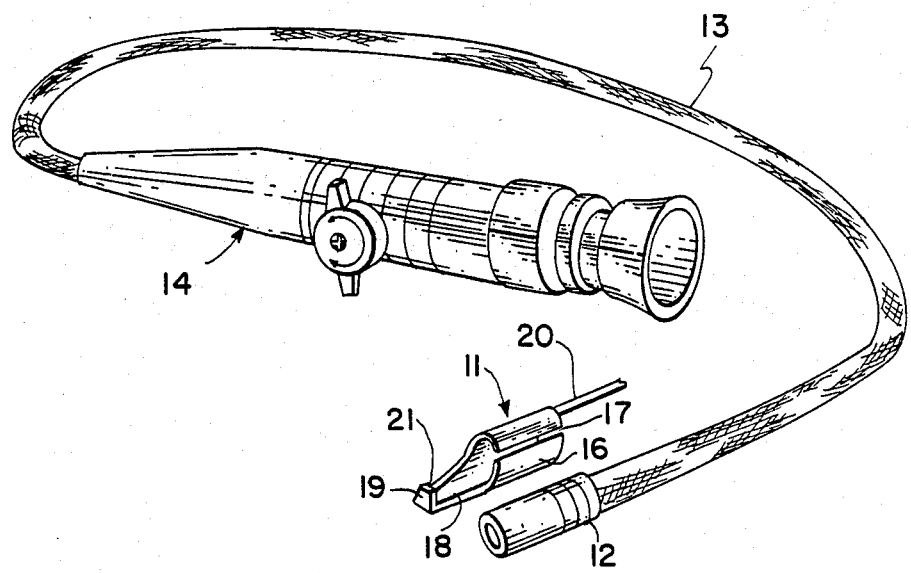
FIG. 1 is a perspective view illustrating a conventional borescope having a flexible extension and an adapter tip in accordance with a preferred embodiment of the invention.
Figure 2:
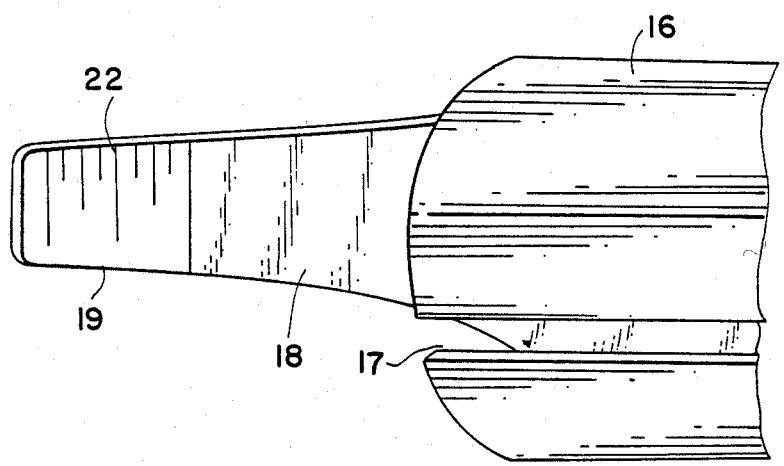
FIG. 2 is an enlarged perspective view illustrating a measuring scale affixed to the adapter tip shown in FIG. 1.

Referring to FIGS. 1 and 2, an adapter tip generally designated by the reference numeral 11 and in accordance with a preferred embodiment of the invention is shown detached from the forward sleeved end 12 of an elongated and flexible extension 13 of a conventional optical borescope 14 that includes focus adjustment means such as a Model IF-11-D1-20 Fiberoptic Borescope made by the Industrial Fiberoptics Division, Olympus Corporation, 4 Nevada Dr., Lake Success, N.Y. 11042.

The adapter tip 11 which may be formed of stainless steel or the like comprises a substantially cylindrical body portion 16 of slightly less diameter than the sleeved end 12 over which it is adapted to be force fit. An elongated slit 17 in the body portion 16 is provided to permit the adapter tip 11 to be securely supported on the sleeved end 12 as well as easily removed without any other attachment means.

An elongated finger 18 integrally formed on the body portion 16 includes a transversely extending tang 19 to the inside face 21 of which a suitable measuring scale 22 is permanently affixed by means of an adhesive or removably secured by suitable fasteners such as screws or the like. The scale 22 may vary in size and measurement indicia—inches or metric for instance—depending upon the visual accuracy of the measurement to be made. It may also vary in shape and be transparent or opaque. The adapter tip may also be provided with a tether 20 that extends externally of the object examined, permitting it to be recovered if it should become detached.

In practice, when the borescope 14 is to be employed to make internal inspections of hollow objects such as pressure vessels or the like having an external opening as is well known, the adapter tip 11 with tether 20 attached is secured on the sleeved end 12 before inserting the flexible extension 13, into the vessel through the external opening.

The extension 13 is then adjusted to bring the scale 22 into the field of view of the borescope 14 when positioned to coincide with the internal surface or defect to be measured. The borescope 14 may then be adjusted using the focus adjustment to bring the scale and object to be measured into focus simultaneously permitting the user to make an external and substantially direct reading of scale 22. This permits visual measurements as accurate as one-half of the smallest division of the scale 22. Internal measurements using an adapter tip 11 in accordance with this invention are substantially as accurate as placing the same scale against the objects being measured.

While a metal adapter tip 11 has been described, it may also be formed of plastic or other suitable material. The scale supporting tang 19 may be formed of a bendable, resilient, spring-like material permitting the forward sleeved end 12 to be inserted through openings, but slightly larger than the sleeved end 12, the bent tang 19 returning to its normal transverse position after passing the narrow opening.

DESCRIPTION OF ALTERNATIVE EMBODIMENTS OF THE INVENTION

Referring to FIGS, 3(a)–(f), numerous different measuring indicia that may be provided by alternative embodiments of the invention are shown, all of such measuring indicia being formed on, in, or by tangs 23–29 extending from fingers 31–37, respectively, that project from a flexible body portion 16 as previously described.

Figure 3:
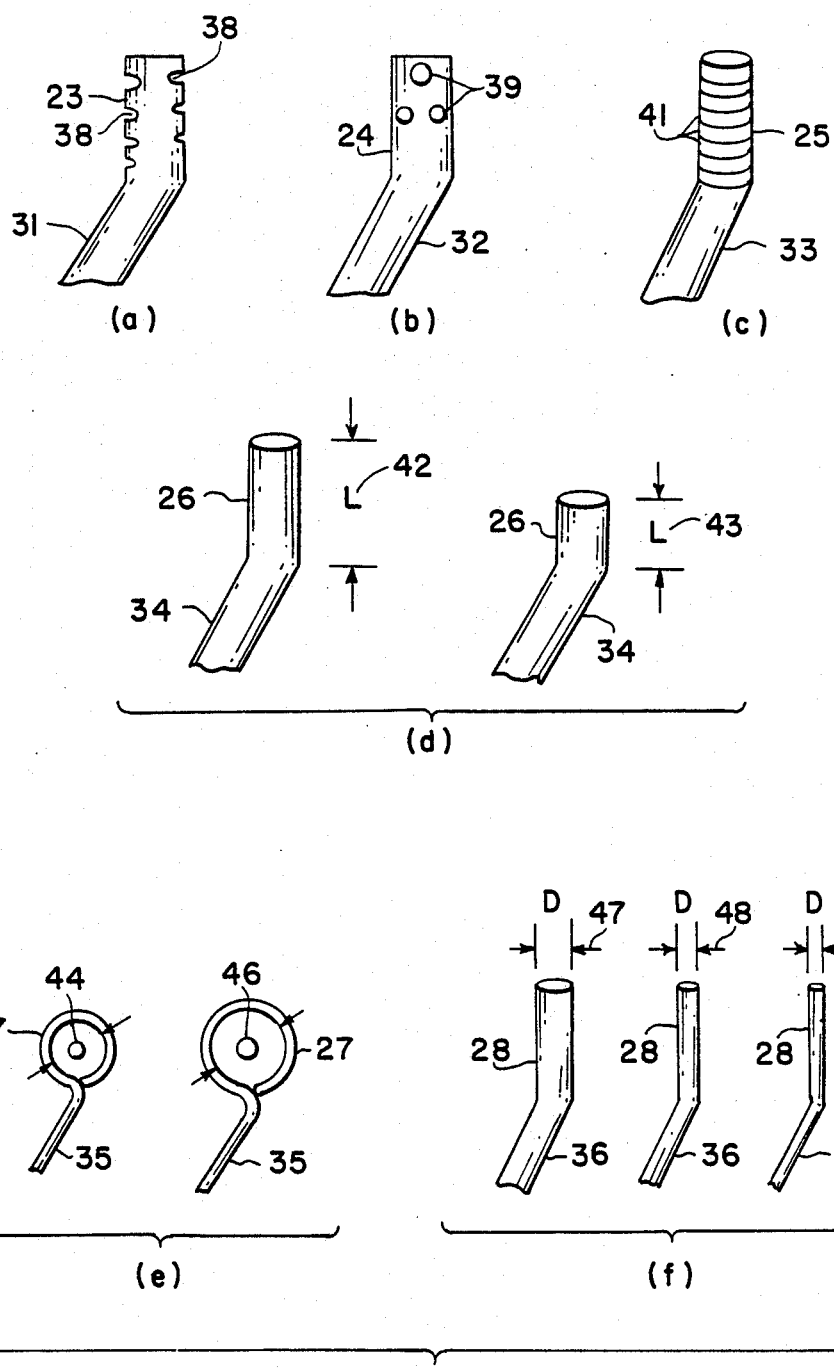
FIGS. 3(a)-(f) illustrate alternative embodiments of an adapter tip and different ways in which the adapter tip may be formed to provide different measuring indicia.

As shown in FIG. 3a, the tang 23 and finger 31 may be formed of a flat, metal, plastic, or rubber-like material, the edges of the tang 23 being provided with notches, slots or other measuring indicia 38 of known dimensions. The tang 24 of finger 32 in the embodiment shown in FIG. 3b is provided with circular or other shaped holes 39 of known dimensions.

As shown in FIG. 3c, the finger 33 and tang 25 may be integrally formed of a wire made of metal, plastic or bendable, resilient material and provided with horizontal gradations or markings 44 of a known scale.

FIG. 3d shows different arrangements of the embodiment shown in FIG. 3c in which the wire fingers 34 and tangs 26 may be of different known lengths (e) 42 and 43.

FIG. 3e shows yet another alternative embodiment of the invention in which wire tangs 27 are integrally formed into circular loops 44 and 46 of known and different dimensions.

FIG. 3f shows yet other alternative embodiments in which the wire forming the fingers 36 and tangs 28 are of different but known diameters (d) 47, 48 and 49 respectively.

While preferred and alternative embodiments of the invention have been described in detail, numerous changes and variations in the means of detachably securing the adapter tip 11 to a remote measuring device and in the type of measuring indicia provided can be made within the principles of the invention which is to be limited only by the scope of the appended claims.

I claim:

1. An adapter tip for the forward end of an optical borescope including focus adjustment means and used for the internal inspection of an object having an external opening therein through which said forward end may be inserted comprising:
    a body portion adapted to be secured to said forward end of said borescope:
    said body portion including means for supporting measuring indicia thereon thereby permitting external, substantially direct measurements when said measuring indicia coincide with an internal surface or defect and both brought into simultaneous focus with said focus adjustment means.

2. The invention as defined in claim 1 wherein said means for supporting said measuring indicia comprises a tang that extends from a finger on said body portion, said measuring indicia being affixed to said tang.

3. The invention as defined in claim 2 wherein said tang and said measuring indicia are formed of a bendable, resilient material.

4. The invention as defined in claim 2 wherein said tang and measuring indicia are formed of a transparent material.

5. The invention as defined in claim 2 wherein a tether is attached to said adapter tip.

6. The invention as defined in claim 2 wherein said measuring indicia are marked n said tang.

7. The invention as defined in claim 2 wherein said measuring indicia are formed by said tang.

8. The invention as defined in claim 7 wherein said measuring indicia are formed in said tang.

9. The invention as defined in claim 7 wherein said measuring indicia are circles integrally formed by said tang.

10. The invention as defined in claim 7 wherein said measuring indicia are determined by the physical dimensions of said tang.

* * * * *